(12) United States Patent
Klaas et al.

(10) Patent No.: US 9,354,149 B2
(45) Date of Patent: May 31, 2016

(54) TEST METHOD, TEST RIGS AND CONTROL SYSTEM

(71) Applicant: Airbus Operations GmbH, Hamburg (DE)

(72) Inventors: Andrej Klaas, Hamburg (DE); Rolf Hinrichs, Hamburg (DE); Andreas Kotzke, Hamburg (DE); Andreas Hofferek, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 212 days.

(21) Appl. No.: 14/036,614

(22) Filed: Sep. 25, 2013

(65) Prior Publication Data

US 2014/0090479 A1   Apr. 3, 2014

Related U.S. Application Data

(60) Provisional application No. 61/706,807, filed on Sep. 28, 2012.

(30) Foreign Application Priority Data

Sep. 28, 2012  (EP) .................................... 12186523

(51) Int. Cl.
*G01N 3/02* (2006.01)
*G01M 5/00* (2006.01)

(52) U.S. Cl.
CPC .............. *G01N 3/02* (2013.01); *G01M 5/0075* (2013.01); *G01N 2203/0023* (2013.01);
(Continued)

(58) Field of Classification Search
CPC . G01M 5/0016; G01M 5/0041; G01M 5/005; G01M 5/0075; G01N 2203/0023; G01N 2203/0048; G01N 2203/0204; G01N 2203/0611; G01N 2203/0617; G01N 3/02; G01N 3/10
USPC ..................................................... 73/788, 802
See application file for complete search history.

(56) References Cited

U.S. PATENT DOCUMENTS 2,340,505 A * 2/1944 Beed ................... G01M 5/0016
73/798
2,505,887 A  5/1950 Edison
(Continued)

FOREIGN PATENT DOCUMENTS

| CN | 101451903 | 6/2009 |
|----|-----------|--------|
| CN | 102680215 | 9/2012 |
| WO | 2009097049 | 8/2009 |

OTHER PUBLICATIONS

European Search Report, Apr. 16, 2013.
(Continued)

*Primary Examiner* — Freddie Kirkland, III
(74) *Attorney, Agent, or Firm* — Greer, Burns & Crain Ltd.

(57) ABSTRACT

A method for load relieving a test object, wherein a load is applied by a multiplicity of hydraulic devices positioned side by side each introducing a partial load into the test object such that the test object has a minimum deflection in an area close to its fixation and a maximum deflection in an area far away from the fixation, wherein the load is reduced sequentially from the maximum deflection to the minimum deflection. A test rig is provided that enables an autonomous and non-synchronical load relief of a test object based on pressure difference. A test rig is provided that enables an autonomous and non-synchronical load relief of a test object based on a delay time and a control system for such test rigs.

12 Claims, 3 Drawing Sheets

(52) U.S. Cl.
CPC .......... *G01N 2203/0048* (2013.01); *G01N 2203/0204* (2013.01); *G01N 2203/0264* (2013.01); *G01N 2203/0611* (2013.01); *G01N 2203/0617* (2013.01)

(56) References Cited

U.S. PATENT DOCUMENTS

| | | | | |
|---|---|---|---|---|
| 3,048,033 | A * | 8/1962 | Melzer | G01M 5/0016 73/802 |
| 3,942,362 | A * | 3/1976 | Keller | G01M 5/005 73/816 |
| 4,453,413 | A * | 6/1984 | Schneider | G01M 5/005 73/802 |
| 6,035,715 | A * | 3/2000 | Porter | G01M 7/02 73/432.1 |
| 7,155,982 | B2 * | 1/2007 | Oesmann | G01N 3/10 73/818 |
| 7,703,335 | B2 * | 4/2010 | DiMartino | G01N 3/02 73/856 |
| 7,715,994 | B1 | 5/2010 | Richards et al. | |
| 8,024,981 | B2 * | 9/2011 | Hinrichs | G01M 5/0041 73/802 |
| 8,474,325 | B1 * | 7/2013 | Schmidgall | G01N 3/08 73/760 |
| 8,621,934 | B2 * | 1/2014 | Hughes | F03D 1/065 73/808 |
| 8,997,324 | B2 * | 4/2015 | Tsuruta | G01M 5/0058 269/218 |
| 2010/0263448 | A1 | 10/2010 | Hughes et al. | |

OTHER PUBLICATIONS

Chinese Office Action, Sep. 6, 2015.

\* cited by examiner

TEST METHOD, TEST RIGS AND CONTROL SYSTEM

CROSS-REFERENCES TO RELATED APPLICATIONS

This application claims the benefit of the U.S. Provisional Application No. 61/706,807, filed on Sep. 28, 2012, and of the European patent application No. 12 186 523.2 filed on Sep. 28, 2012, the entire disclosures of which are incorporated herein by way of reference.

BACKGROUND OF THE INVENTION

The invention concerns a method for load relieving a test object, test rigs for load testing a test object, in particular for the execution of such a method, and a control system for a test rig.

In structural tests a load is applied to a structural element in a test. A known test rig comprises a multiplicity of hydraulic means positioned side by side, each introducing a partial load into the structural element such that it has a minimum deflection at its area close to a clamping device in which the structural element is fixed, and a maximum deflection at its area far away from the clamping device. In case of an emergency shutdown, a load distribution can appear that exceeds a load capacity of the structural element. In order to avoid this scenario, a control system is provided which ensure a synchronical relief of the hydraulic means in a same ratio. In one known method, a relief is achieved by pressure balancing both pressure chambers of each hydraulic means, whereby the hydraulic means are reset independently from each other. In another known method which is similar to the afore-mentioned method, the hydraulic means are reset by adjustable throttles such that the load ratio between the hydraulic means remains equal. In a third known method, a redundant independent device for relieving the test object is used.

SUMMARY OF THE INVENTION

The object of the invention is to create a method for load relieving a test object, which enables a fast and reliable load relief without damaging the test object, test rigs for load testing a test object enabling a fast and reliable relieving without damaging the test object and in particular for the execution of such a method, and also a control system for such a test rig.

In an inventive method for load relieving a test object, wherein a load is supplied by a multiplicity of hydraulic means positioned side by side, each introducing a partial load into the test object such that the test object has a minimum deflection in an area close to its fixation and a maximum deflection far away in an area close to the fixation, the load is reduced sequentially from the maximum deflection to the minimum deflection.

The method enables an autonomous and non-synchronical fast and reliable relieving of a test object wherein by starting at an outer test object area and ending at an inner test object area the load and the deflection respectively is reduced step-by-step. Hereby, an overloading and thus a damage of the test object in the case of an emergency shutdown are avoided.

In one embodiment, a hydraulic means close to a clamping device is reset as a function of the pressure difference of an adjacent hydraulic means far away from the clamping device. The close hydraulic means is reset not before the different pressure of the far hydraulic means falls under a preliminary minimum pressure value. Hereby, a separate control unit can be avoided for deactivating and resetting respectively the hydraulic means so that such a method is reliable operated by its own.

According to a hydro dynamical alternative, the pressure difference is measured hydraulically. The hydraulical measurement has the advantage that no current supply is needed for load relieving the test object. Even if the current supply of the test rig breaks down, a reliable load relieving takes place. Thus, this alternative is highly fail-proof.

According to a hydro electrical alternative, the pressure difference is measured electronically. This alternative is cheaper than the aforementioned hydraulic alternative; however a current supply has to be provided.

In a further alternative, the hydraulic means are reset sequentially after a delay time. The delay time can be determined experimentally and covers such a time period that even if the resetting of the hydraulic means far away from the clamping device takes an unusually long time, the adjacent hydraulic means close to the clamping device won't be reset before the predetermined minimum pressure value has been reached.

An inventive test rig for load testing a test object, in particular for the execution of an inventive method, comprises a clamping device for fixing the test object and a multiplicity of hydraulic means positioned side by side for introducing a partial load into the test object each. The test rig further comprises at least one control system for measuring a pressure difference between pressure chambers of a hydraulic means far away from the clamping device and for resetting an adjacent hydraulic means close to the clamping device as a function of the pressure difference.

Such a test rig ensures a reliable load relieving, is easy to install and cost effective.

In one embodiment the at least one control system comprises a pressure difference activated control valve and a bypass valve for pressure balancing the pressure in the pressure chambers of the hydraulic means close to the clamping device which is in operative connection with the pressure difference activated control valve. Such a control system works autonomous and in particular without any electrical components. Thus, a current supply can be omitted.

In an alternative the at least one control valve is activated by a hydraulic comparator means. By means of the hydraulic comparator, hydraulic instabilities of the pressure difference are eliminated such that the minimum pressure value can be set accurately.

In another alternative, the at least one control system comprises an electronic pressure difference activated control unit and a bypass valve for pressure balancing the pressure in the pressure chambers in the hydraulic means close to the clamping device which is an operative connection with the electronic pressure difference activated control unit. This alternative is cheaper than the aforementioned hydraulic alternative; however a current supply has to be provided.

A further inventive test rig for load testing a test object, in particular for the execution of an inventive method, comprises a clamping device for fixing the test object and a multiplicity of hydraulic means positioned side by side for introducing a partial load into the test object each. Further on, the test rig comprises at least a control system for resetting a hydraulic means close to the clamping device after a delay time of resetting a respective adjacent hydraulic means far away from the clamping device.

Such a test rig is easy to install, cost-effective and highly reliable, as only a few technical, in particular electrical, components are needed.

Preferably the control unit comprises a time activated bypass valve for pressure balancing the hydraulic means close to the clamping device. Only a signal line for transmitting the time signal is needed for activating the bypass valve.

Additionally, an inventive control system is provided which measures a pressure difference between pressure chambers of a hydraulic means far away from a clamping device and for resetting an adjacent hydraulic means close to the clamping device as a function of the pressure difference, or for resetting a hydraulic means close to a clamping device after a delay time of resetting a respective adjacent hydraulic means far away from the clamping device.

Such control systems enables a fast and reliable load relief of a test object without damaging the test object.

Other advantage examples of the embodiment of the invention are the subject of further subsidiary claims.

BRIEF DESCRIPTION OF THE DRAWINGS

In what follows preferred examples of embodiment of the invention are elucidated in more detail with the help of schematic representations. Here.

DETAILED DESCRIPTION OF THE PREFERRED EMBODIMENTS

Figure 1:
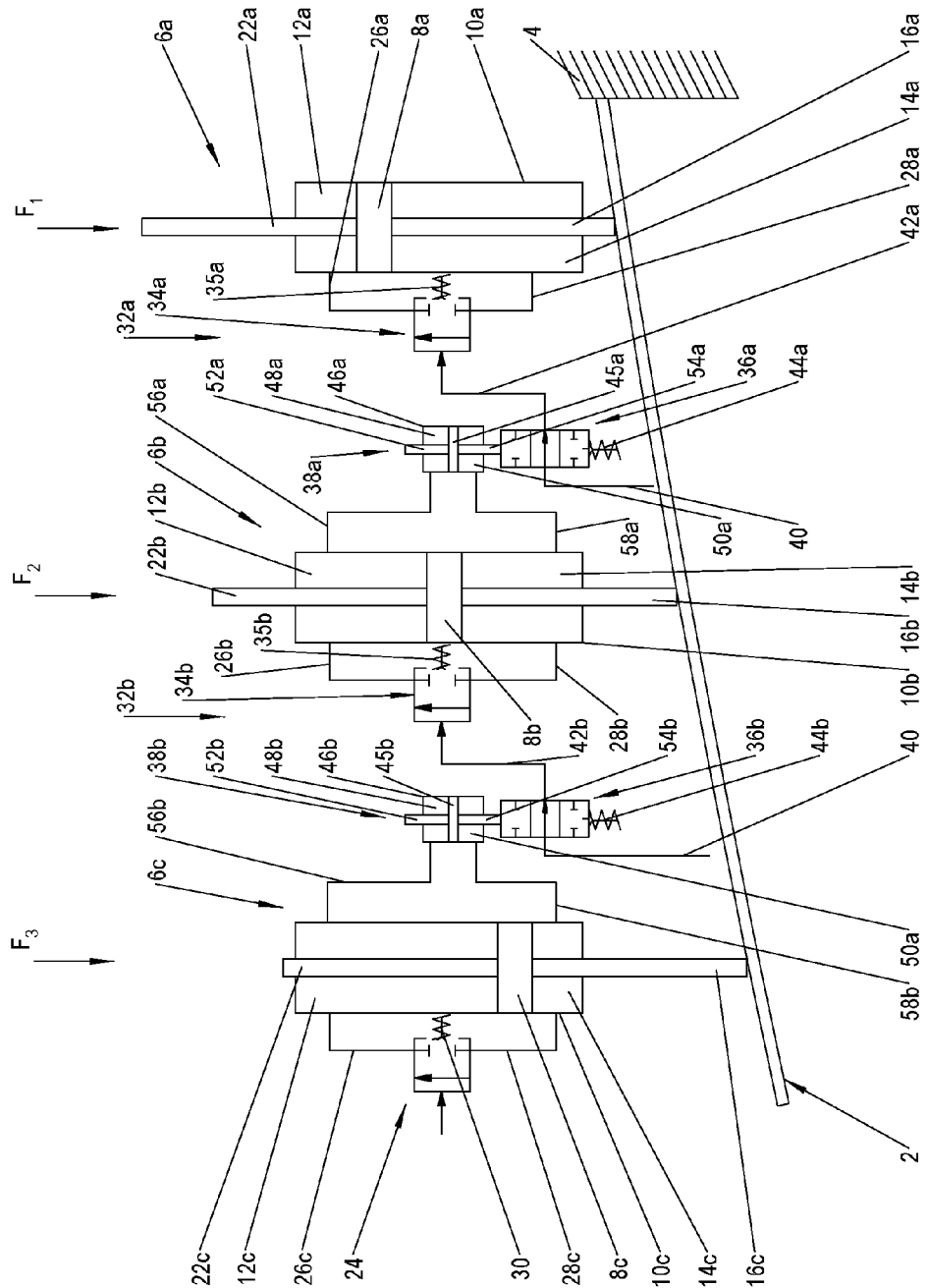
FIG. 1 shows a first schematic embodiment of an inventive test rig.

In FIG. 1, a test rig 1 for applying a load to test object 2 and for load relieving the test object, in particular in the case of an emergency, is shown. The test object 2 is a structural element of an aircraft such as a longitudinal stiffening element, for instance. It is fixed in a clamping device 4 of the test rig 1 and has in relation to the clamping device 4 an inner area, a center area and an outer area. The outer area is the object area which is farthest away from the clamping device 4 and the inner are is the object area which is closest to the clamping device 4.

The test rig 1 comprises in the shown embodiment a first, a second and a third hydraulic means 6a, 6b, 6c for applying a load to the test object 2 in a direction which is vertical to the longitudinal direction of the test object. The hydraulic means 6a, 6b, 6c are positioned side by side, wherein each hydraulic means 6a, 6b, 6c introduces a partial load F1, F2, F3 into the test object 2. The partial loads F1, F2, F3 are such applied to the test object 2 that the test object 2 has a minimum deflection in its inner area close to the clamping device 4 and a maximum deflection in its outer area far away from the clamping device 4.

Each hydraulic means 6a, 6b, 6c comprises a piston 8a, 8b, 8c which is moveably guided in a cylinder 10a, 10b, 10c and which divides the cylinder 10a, 10b, 10c into two pressure chambers 12a, 14a and 12b, 14b and 12c, 14c respectively. Each piston 6a, 6b, 6c is connected with a front piston rod 16a, 16b, 16c which intersects the cylinder 10a, 10b, 10c at its front side faced to the test object 2 and which can be pressed against the test object 2 by pressurizing the rear pressure chamber 12a, 12b, 12c. In order to move the pistons 8a, 8b, 8c backwards, the respective front pressure chamber 14a, 14b, 14c is pressurized. In order to provide each piston 8a, 8b, 8c with two opposite pressure effective surfaces 18, 20 of the same size, a rear piston rod 22a, 22b, 22c having the same outer diameter as the front piston rod 16a, 16b, 16c extends from the piston 8a, 8b, 8c and intersects the cylinder 10a, 10b, 10c at its rear side.

The third hydraulic means 6a has a bypass valve 24 for pressure balancing the pressure chambers 12c, 14c. The bypass valve 24 is connected respectively with one of pressure chambers 12c, 14c by pressure lines 26c, 28c. The bypass valve 24 is biased by a spring 30 in its shown closing direction in which a fluid connection between the pressure chambers 12c, 14c is closed. By applying an opening force to the bypass valve 24, the bypass valve 24 is brought in its opening position against the spring force in which the fluid connection is opened and the pressure chambers 12c, 14c are balanced such that the piston 8a can move upwards only by a relief force of the test object 2 due to its elastic deformation. The opening force is applied manually or automatically in the case of an emergency.

In order to enable a fast load relief of the test object 2 hydro dynamical control systems 32a, 32b are provided. Each control system 32a, 32b measures a pressure difference between the pressure chambers 12c, 14c and 12b, 14b respectively of an outer cylinder 10c and 10b respectively and resets an adjacent inner cylinder 10b and 10a respectively as a function of the pressure difference. In the shown embodiment showing three hydraulic means 6a, 6b, 6c, two control systems 32a, 32b are provided, wherein one control system 32b is related to the third and to second hydraulic means 6c, 6b and one control system 32a is related to the second and to the first hydraulic means 6b, 6a.

Each control system 32a, 32b comprises a bypass valve 34a, 34b, a control valve 36a, 36b, and a hydraulic comparator 38a, 38b.

The bypass valves 34a, 34b are pressure activated. They are connected with one of pressure chambers 12a, 14a and 12b, 14b respectively by pressure lines 26a, 28a and 26b, 28b respectively. The bypass valves 34a, 34b are biased by a spring 35a, 35b in their shown closing direction in which a fluid connection between the pressure chambers 12a, 14a and 12b, 14b respectively is closed. By applying an opening force to the bypass valves 34a, 34b they are moved in their opening positions against the spring force in which the fluid connection is opened and the pressure chambers 12a, 14a and 12b, 14b respectively are balanced such that the respective piston 8a, 8b can move upwards only by a relief force of the test object 2 due to the elastic deformation of the test object 2.

The control valves 36a, 36b are provided for applying the opening force to the bypass valves 32. They are 2port/3way-valves having two ports, two closing positions and one opening position. One port is in fluid connection with a pressure line 40. The other port is in fluid connection with the respective bypass valve 34a, 34b via a signal line 42a, 42b. Each control valve 36a, 36b is biased by a spring 44a, 44b in its opening position in which the pressure line 40 is fluid connected with the signal line 42a, 42b and thus the opening force for moving the respective bypass valve 34a, 34b in its opening position is applied. In this status, the respective pressure chambers 12a, 14a, 12b, 14b are pressure balanced. In the lower closing position, the pressure in the rear pressure chambers 14a, 14b is higher than in the front pressure chamber 12a, 12b. In the upper closing position, the pressure in the rear pressure chambers 14a, 14b is lower than in the front pressure chamber 12a, 12b. In both closing positions, the fluid connection between the pressure line 40 and the signal line 42a, 42b is interrupted.

The comparators 38a, 38b are in particular for eliminating pressure difference instabilities. Each comparator 38a, 38b generates a counter force to the spring force of the control valves 36a, 36b. Each comparator 38a, 38b comprises a piston 45a, 45b which is moveably guided in a cylinder 46a, 46b and which divides the cylinder 46a, 46b into two cylinder chambers 48a, 50a and 48b, 50b. Each piston 34 has two opposite piston rods 52a, 54a and 52b, 54b respectively of the same outer diameter that intersect the cylinder 46a, 46b at their opposite sides. The cylinder chambers 48a, 50b, 48b, 50b are fluid connected with one of the pressure chambers 12a, 14a and 12b, 14b respectively by control lines 56a, 58a and 56b, 58b respectively.

In the case of an emergency shutdown, the load is reduced sequentially and non-synchronically from the maximum deflection to the minimum deflection of the test object 2. Therefore, at the beginning of the load relief, the third hydraulic means 6c positioned in the outer area is reset, than the second hydraulic means 6b positioned in the center area is reset and finally the first hydraulic means 6a positioned in the inner area is reset.

First, an opening signal is applied manually or automatically to the bypass valve 24 such that the third cylinder 10c is pressure balanced and its piston 8c moves backwards such that the partial load F3 is reduced to zero and the maximum deflection in the outer area of the test object 2 is eliminated. If the pressure difference between the pressure chambers 12c, 14c falls to a minimum pressure value, preferably if the pressure chambers 12c, 14c are balanced and the pressure value is zero, the control valve 36b is opened and an hydraulic or pneumatic opening signal is applied to the bypass valve 34b of the second cylinder 10b such that the second cylinder 10b is pressure balanced and its piston 8b moves backward. Thus, the partial load F2 is reduced to zero and the deflection in the center area of the test object 2 is eliminated. If the pressure difference between the pressure chambers 12b, 14b of the second hydraulic means 6b falls to a minimum pressure value, preferably if the pressure chambers 12c, 14c are balanced and the pressure value is zero, the control valve 36a is opened and an hydraulic or pneumatic opening signal is applied to the bypass valve 34a of the first cylinder 10a such that the first cylinder 10a is pressure balanced and its piston 8a moves backwards. Thus, the partial load F1 is reduced to zero and the deflection in the inner area of the test object 2 is eliminated. As a result, the test object 2 is load relieved.

In other words, as the test object 2 has its maximum deflection far from the clamping device 4 and its minimum deflection close to the clamping device 4, the load is relieved by balancing the outer hydraulic means 6c and 6b respectively and then by balancing the respective adjacent inner hydraulic means 6b, 6c. In a first relieving step the outer hydraulic means 6c is the third hydraulic means 6c as this is farthest away from the clamping device 4 and the inner hydraulic means is the second hydraulic means 6b as this is adjacent to the outer hydraulic means 6b. In a second relieving step the outer hydraulic means is the second hydraulic 6b as this is now farthest away from the clamping device 4 and the inner hydraulic means is the first hydraulic means 6a.

Figure 2:
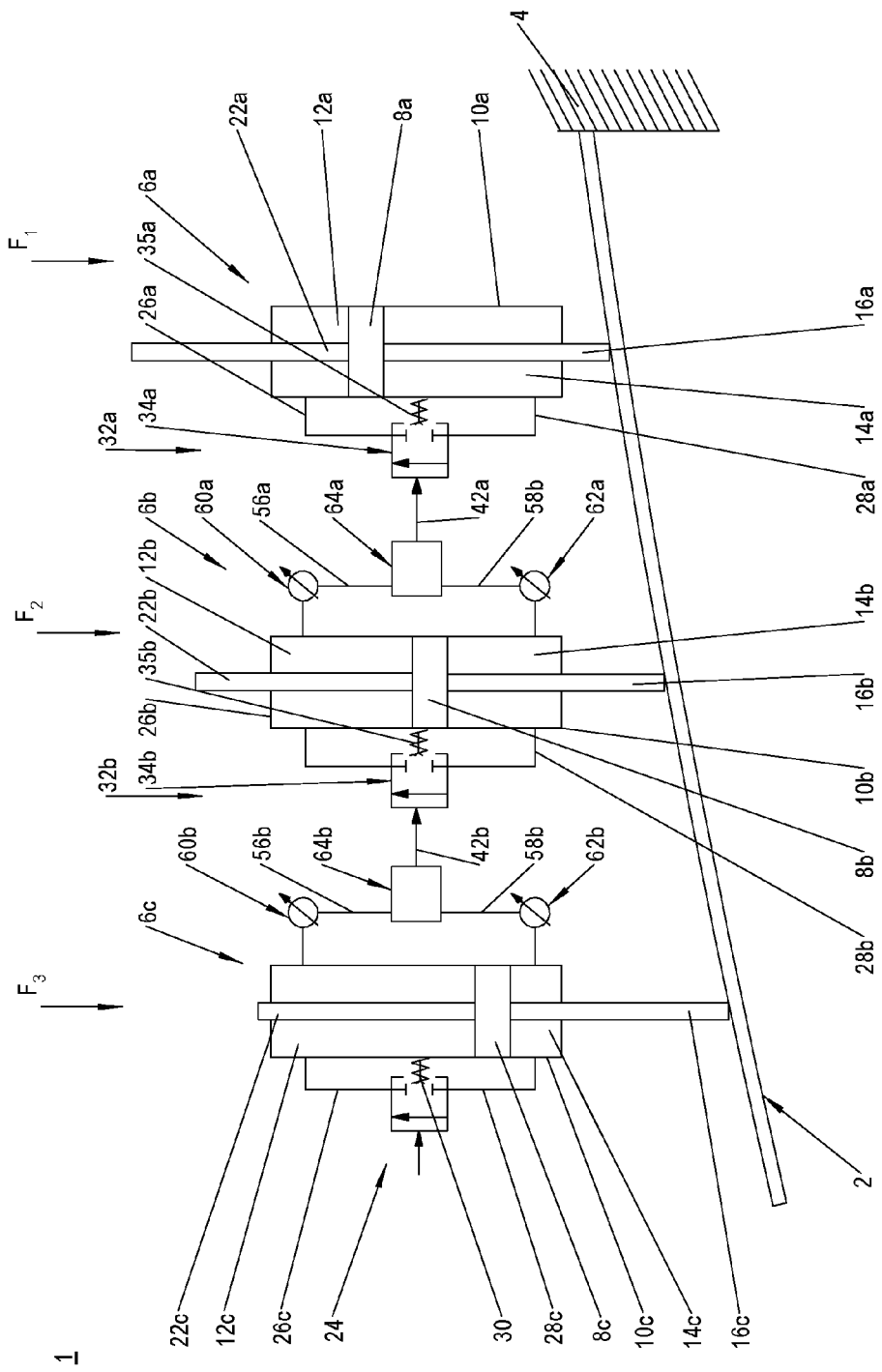
FIG. 2 shows a second schematic embodiment of an inventive test rig.

In FIG. 2 a second embodiment of the inventive test rig 1 is shown.

According to the second embodiment, hydro electrical control systems 32a, 32b are provided. Therefore, each control system 32a, 32b has two pressure sensors 60a, 62a and 64a, 64b respectively for measuring a pressure in the pressure chambers 12b, 14b and 12c, 14c respectively of the hydraulic means 6b, 6c. Further on, they have an electrical control unit 64a, 64b each calculating a pressure difference between the pressure chambers 12b, 14b and 12c, 14c respectively based on the pressure values measured by the pressure sensors 60a, 62a and 60b, 62b respectively and then generating an opening force in order to bring their bypass valves 34a, 34b from their closing position to their opening position.

Contrary to the bypass valves 34a, 34b according to the first embodiment in FIG. 1, the bypass valves 34a, 34b in the second embodiment are activated by an electrical signal which is generated as a function of a pressure difference.

In the case of an emergency shutdown, the load is also reduced sequentially and non-synchronically from the maximum deflection to the minimum deflection of the test object 2. Therefore, at the beginning of the load relief, the third hydraulic means 6c positioned in the outer area is reset, then the second hydraulic means 6b positioned in the center area is reset and finally the first hydraulic means 6a positioned in the inner area is reset.

First, an opening signal is applied to a bypass valve 24 of the third hydraulic means 6c such that the third cylinder 10c is pressure balanced and its piston 8c moves backwards such that the partial load F3 is reduced to zero and the maximum deflection in the outer area of the test object 2 is eliminated. If the pressure difference between the pressure chambers 12c, 14c of the third hydraulic means 6c calculated by the control unit 64b falls to a minimum pressure value, preferably if the pressure chambers 12c, 14c are balanced and the pressure value is zero, the control unit 64b generates an opening signal to the bypass valve 34b of the second cylinder 10b such that the second cylinder 10b is pressure balanced and its piston 8b moves backward. Thus, the partial load F2 is reduced to zero and the deflection in the center area of the test object 2 is eliminated. If the pressure difference between the pressure chambers 12b, 14b of the second hydraulic means 6b calculated by the control unit 64a falls to a minimum pressure value, preferably if the pressure chambers 12b, 14b are balanced and the pressure value is zero, the control unit 64a generates an opening signal to the bypass valve 34a of the first cylinder 10a such that the first cylinder 10a is pressure balanced and its piston 8a moves backwards. Thus, the partial load F1 is reduced to zero and the deflection in the inner area of the test object 2 is eliminated. As a result, the test object 2 is load relieved.

Again, as the test object 2 has its maximum deflection far away from the clamping device 4 and its minimum deflection close to the clamping device 4, the load is relieved by balancing the outer hydraulic means 6c and 6b respectively and then by balancing the respective adjacent inner hydraulic means 6b, 6c. In a first relieving step the outer hydraulic means 6c is the third hydraulic means 6c as this is farthest away from the clamping device 4 and the inner hydraulic means is the second hydraulic means 6b as this is adjacent to the outer hydraulic means 6b. In a second relieving step the outer hydraulic means is the second hydraulic 6b as this is now farthest away from the clamping device 4 and the inner hydraulic means is the first hydraulic means 6a.

Figure 3:
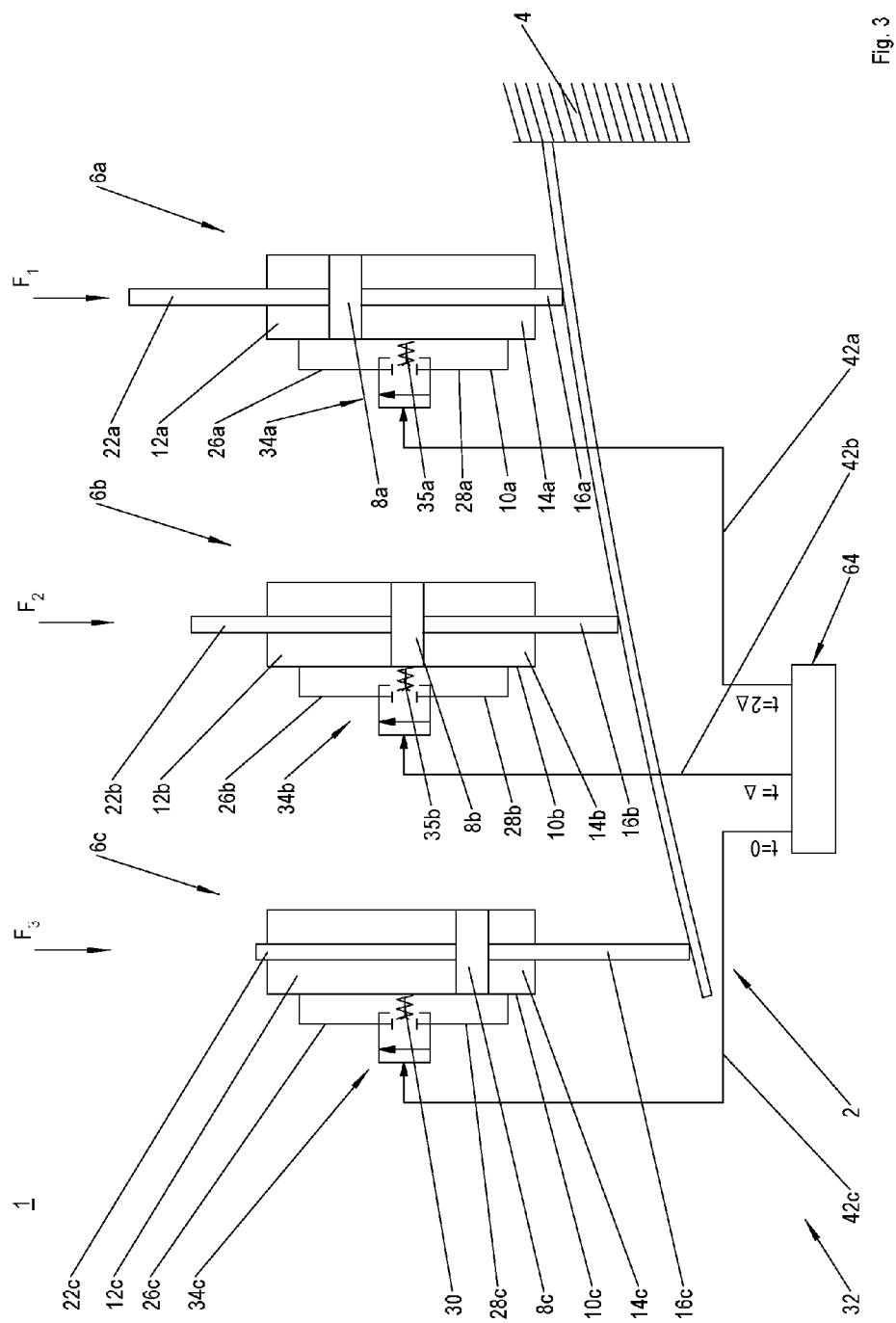
FIG. 3 shows a third schematic embodiment of an inventive test rig.

In FIG. 3 a third embodiment of the inventive test rig 1 is shown.

According to the third embodiment, a control system 32 is provided having one electrical control unit 64 and several bypass valves, 34a, 34b, 34c for an emergency shutdown of hydraulic means 6a, 6b, 6c. In relation to the shown three hydraulic means 6a, 6b, 6c three bypass valves 34a, 34b, 34c are provided which are in signal connection with the control unit 64.

Contrary to the bypass valves 34a, 34b according to the second embodiment in FIG. 2, the bypass valves 34a, 34b, 34c in the third embodiment are activated by an electrical signal which is generated after a predetermined period of time and delay time t respectively. Thus, the bypass valves 34a, 34b, 34c are time activated valves. They are connected respectively with one of the pressure chambers 12a, 14a, 12b, 14b, 12c, 14c by pressure lines 26a, 28a and 26b, 28b and 26c, 38c respectively. The bypass valves 34a, 34b, 34c are biased by a spring 35a, 35b, 35c in their shown closing direction in which a fluid connection between the pressure chambers 12a, 14a and 12b, 14b and 12c, 14c respectively is closed. By applying an opening force to the bypass valves 34a, 34b, 34c they are moved in their opening positions against the spring force in which the fluid connection is opened and the pressure chambers 12a, 14a and 12b, 14b and 12c, 14c respectively are balanced such that the respective piston 8a, 8b, 8c can move upwards only by a relief force of the test object 2 due to its elastic deformation.

The control unit 64 covers a timer for generating the opening signal (opening force) after the delay time Δt. The delay time t is a period of time between the pressure balancing of two adjacent hydraulic means 6a, 6b, 6c. Preferably, the delay time t is constant. The control unit 64 is electrical connection with each bypass valves 34a 34b, 34c via one signal lines 42a, 42b, 42c. The delay time for generating the opening signal can be determined experimentally.

In the case of an emergency shutdown, the load is also reduced sequentially and non-synchronically from the maximum deflection to the minimum deflection of the test object 2. Therefore, at the beginning of the load relief, the third hydraulic means 6c positioned in the outer area is reset, then the second hydraulic means 6b positioned in the center area is reset and finally the first hydraulic means 6a positioned in the inner area is reset.

First, the control unit 64 generates at the delay time t=0 an opening signal which is applied to the bypass valve 34c of the third hydraulic means 6c such that the third cylinder 10c is pressure balanced and its piston 8c moves backwards such that the partial load F3 is reduced to zero and the maximum deflection in the outer area of the test object 2 is eliminated. Second, after the delay time t=Δ, the control unit 64 generates an opening signal which is applied to the bypass valve 34b of the second hydraulic means 6b such that the second cylinder 10b is pressure balanced and its piston 8b moves backwards. Thus, the partial load F2 is reduced to zero and the deflection in the center area of the test object 2 is eliminated. Third, after the same delay time t=Δ, and thus twice the delay time t=2Δt measured from the third hydraulic means 6c, the control unit 64 generates an opening signal which is applied to the bypass valve 34a of the first hydraulic means 6a such that the first cylinder 10a is pressure balanced and its piston 8a moves backwards. Thus, the partial load F1 is reduced to zero and the deflection in the inner area of the test object 2 is eliminated. As a result, the test object 2 is load relieved.

Again, as the test object 2 has its maximum deflection far away from the clamping device 4 and its minimum deflection close to the clamping device 4, the load is relieved by balancing the outer hydraulic means 6c and 6b respectively and then by balancing the respective adjacent inner hydraulic means 6b, 6c. In a first relieving step the outer hydraulic means 6c is the third hydraulic means 6c as this is farthest away from the clamping device 4 and the inner hydraulic means is the second hydraulic means 6b as this is adjacent to the outer hydraulic means 6b. In a second relieving step the outer hydraulic means is the second hydraulic means 6b as this is now farthest away from the clamping device 4 and the inner hydraulic means is the first hydraulic means 6a.

Disclosed is a method for load relieving a test object, wherein a load is applied by a multiplicity of hydraulic means positioned side by side, each introducing a partial load into the test object such that the test object has a minimum deflection in an area close to its fixation and a maximum deflection in an area far away from the fixation, wherein the load is reduced sequentially from the maximum deflection to the minimum deflection, a test rig that enables an autonomous and non-synchronical load relief of a test object based on pressure difference, a test rig that enables an autonomous and non-synchronical load relief of a test object based on a delay time and a control system for such test rigs.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

REFERENCE SYMBOL LIST 1 test rig
2 test object
4 clamping device
6a, 6b, 6c hydraulic means
8a, 8b, 8c piston
10a, 10b, 10c cylinder
12a, 12b, 12c rear pressure chamber
14a, 14b, 14c front pressure chamber
16a, 16b, 16c front piston rod
18 effective surface
20 effective surface
22a, 22b, 22c rear piston rod
24 bypass valve
26a, 26b, 26c pressure line
28a, 28b, 28c pressure line
40 spring
32, 32a, 32b control system
34a, 34b, 34c bypass valve
35a, 35b, 35c spring
36a, 36b control valve
38a, 38b comparator
40 pressure line
42a, 42b signal line
44a, 44b spring
45a, 45b piston
46a, 46b cylinder
48a, 48b cylinder chamber
50a, 50b cylinder chamber
52a, 52b piston rod
54a, 54b piston rod
56a, 56b control line
58a, 58b control line
60a, 60b pressure sensor
62a, 62b pressure sensor
64, 64a, 64b control unit
F1, F2, F3 partial load

The invention claimed is:

1. A method for load relieving a test object, wherein a load is applied by a multiplicity of hydraulic means positioned side by side, each introducing a partial load into the test object such that the test object has a minimum deflection in an area close to its fixation and a maximum deflection in an area far away from the fixation, comprising the step of reducing the load sequentially from the maximum deflection to the minimum deflection.

2. The method according to claim 1, including the step of resetting a hydraulic means close to a clamping device as a function of a pressure difference of an adjacent hydraulic means far away from the clamping device.

3. The method according to claim 2, wherein the pressure difference is measured hydraulically.

4. The method according to claim 2, wherein the pressure difference is measured electronically.

5. The method according to claim 1, wherein the hydraulic means are reset sequentially after a delay time.

6. A test rig for load testing a test object, comprising:
a clamping device for fixing the test object,
a multiplicity of hydraulic means positioned side by side for each introducing a partial load into the test object, and
at least one control system for measuring a pressure difference between pressure chambers of a hydraulic means far away from the clamping device and for resetting an adjacent hydraulic means close to the clamping device as a function of the pressure difference.

7. The test rig according to claim 6, wherein the at least one control system comprises a pressure difference activated control valve and a bypass valve for pressure balancing the pressure in the pressure chambers of the hydraulic means close to the clamping device which is in operative connection with the pressure difference activated control valve.

8. The test rig according to claim 7, wherein the at least one control valve is activated by a hydraulic comparator.

9. The test rig according to claim 6, wherein the at least one control system comprises an electronic pressure difference activated control unit and a bypass valve for pressure balancing the pressure in the pressure chambers of the hydraulic means close to the clamping device which is in operative connection with the electronic pressure difference activated control unit.

10. A control system for a test rig according to claim 6.

11. A test rig for load testing a test object, comprising:
a clamping device for fixing the test object,
a multiplicity of hydraulic means positioned side by side for each introducing a partial load into the test object, and
at least one control system for resetting a hydraulic means close to the clamping device after a delay time of resetting an adjacent hydraulic means far away from the clamping device.

12. The test rig according to claim 11, wherein the control unit comprises a time activated bypass valve for pressure balancing the hydraulic means close to the clamping device.

* * * * *